US006262309B1

(12) United States Patent
Fukada et al.

(10) Patent No.: US 6,262,309 B1
(45) Date of Patent: Jul. 17, 2001

(54) PROCESS FOR PRODUCING NORBORNANE DIMETHYLENE AMINES

(75) Inventors: Isao Fukada, Mobara; Seiichi Ishii, Ichihara; Hiroharu Kageyama, Mobara; Hiroki Mizutani, Tokyo, all of (JP)

(73) Assignee: Mitsui Chemicals, Inc. (JP)

(*) Notice: Subject to any disclaimer, the term of this patent is extended or adjusted under 35 U.S.C. 154(b) by 0 days.

(21) Appl. No.: 09/667,801

(22) Filed: Sep. 22, 2000

(30) Foreign Application Priority Data

Sep. 27, 1999 (JP) .................................................. 11-271542

(51) Int. Cl.⁷ .................................................. C07C 209/00
(52) U.S. Cl. ............................................ 564/448; 564/456
(58) Field of Search ...................................... 564/448, 456

(56) References Cited

U.S. PATENT DOCUMENTS 5,087,722 * 2/1992 Inomata ................................ 558/338

FOREIGN PATENT DOCUMENTS

| 54-40524 | 12/1979 | (JP) . |
| 152381 | 11/1989 | (JP) . |
| 03081255 | 4/1991 | (JP) . |
| 03109361 | 5/1991 | (JP) . |
| 04282347 | 10/1992 | (JP) . |
| 2713612 | 10/1997 | (JP) . |
| 2713615 | 10/1997 | (JP) . |
| 2713623 | 10/1997 | (JP) . |

* cited by examiner

*Primary Examiner*—Samuel Barts
(74) *Attorney, Agent, or Firm*—Burns, Doane, Swecker, & Mathis, L.L.P.

(57) ABSTRACT

Disclosed is a process for producing norbornane dimethylene amines wherein norbornane dicarbonitriles are hydrogenated by using a Raney cobalt catalyst containing manganese etc. in the presence of water in an amount of 0.1 to 1.5 moles per mole of the norbornane dicarbonitriles.

26 Claims, No Drawings

PROCESS FOR PRODUCING NORBORNANE DIMETHYLENE AMINES

BACKGROUND OF THE INVENTION

1. Field of the Invention

The present invention relates to a process for producing norbornane dimethylene amines (bicyclo[2.2.1]heptane bis (methylamine)'s) by hydrogenating norbornane dicarbonitriles (bicyclo[2.2.1]heptane dicarbonitriles).

2. Description of the Related Art

Heretofore, it has been known that diamines are produced by hydrogenating dinitriles in the presence of a metal catalyst such as cobalt, nickel or platinum, but the present situation is that the preferable reaction conditions, reaction yields etc. are greatly varied depending on the type of individual dinitriles and thus the process fails to satisfy industrial production levels.

As a method of producing norbornane dimethylene amines by hydrogenating norbornane dicarbonitriles, a method of using a Raney cobalt catalyst (Japanese Patent No. 2713612) or a method of using a Raney nickel catalyst (Japanese Patent No. 2713615), in the presence of an organic solvent and ammonia, are known.

In connection with the foregoing, it is known that when a cobalt-carried catalyst having cobalt carried on a carrier such as silica, alumina or silica-alumina is used, the catalyst can maintain its activity for a prolonged period of time and thus can be repeatedly used several times (Japanese Patent No. 2713623).

Although the catalyst is re-usable in the method described in Japanese Patent No. 2713623 supra, it cannot be said in consideration of industrial production that the number of times the catalyst can be repeatedly used is sufficient, and thus a considerable amount of the catalyst is still required in production of norbornane dimethylene amines by hydrogenation of norbornane dicarbonitriles. Further, because of requiring not only a large amount of the catalyst but also high costs in the disposal of the used catalyst or in the process of regeneration of the catalyst, this method needs further improvement in order to achieve economical and industrial production of norbornane dimethylene amines.

Meanwhile, Japanese patent publication No. (JP-B) 1-52381 has reported a method of hydrogenating aliphatic nitriles, alkylene oxynitriles or alkylene aminonitriles into primary amines wherein the hydrogenation is carried out using a cobalt or ruthenium catalyst in an ammonia-containing ether solvent and in the presence of water in an amount ranging about 5 to 15% by volume of the ether solvent, whereby the life of the catalyst is prolonged about twice as long as that of the catalyst in the absence of water.

However, the type of dinitrile used in the method described in the above publication is different from the type of dinitrile used as the starting material in the present invention, and further even if the life of the catalyst is improved, its life is still not satisfactory. In addition, it is shown therein that the ether solvent is required in an amount of about 75 to 95% by weight relative to the starting nitrile while water is required in an amount of about 20 to 300% by weight relative to the starting nitrile in order to achieve a sufficient yield of the primary amines to be produced.

That is, in the method described in JP-B 1-52381 supra, the solvent and water are used in large amounts relative to the starting nitrile so that the productivity of the desired primary amines is lowered and enormous energy is necessary for separation or recovery of the solvent and water after the reaction. Hence, this prior art cannot be deemed to be a method capable of producing the product efficiently, economically and inexpensively on the industrial scale.

Further, Japanese patent publication No. (JP-B) 54-40524 discloses production of tetramethylene diamine by hydrogenating succinonitrile wherein the reaction is carried out in the presence of a Raney cobalt catalyst containing manganese. It is described in the Examples therein that the catalyst was able to be used repeatedly up to 50 times in the hydrogenation reaction.

However, the type of dinitrile described in the publication mentioned above is different from the starting material used in the present invention, and even if the catalyst can be used repeatedly, this result could be achieved under those conditions where the catalyst, a solvent and ammonia are used in very large amounts, that is, the amount of metal cobalt as the catalyst is 39% by weight, the amount of dioxane used as the solvent is 600% by weight, and the amount of liquid ammonia used is 600% by weight each ralative to the starting material, succinonitrile.

That is, in view of the amount of the catalyst used, the number of times the catalyst can be repeatedly used can be evaluated to be insufficient in the method described in JP-B 54-40524 supra. Further, this method is a method in which not only the catalyst but also the solvent and liquid ammonia are used in large amounts relative to the starting succinonitrile, so that the productivity of the desired tetramethylene diamine is lowered and enormous energy is necessary for separation or recovery of the used solvent and ammonia after the reaction. Hence, this prior art cannot be deemed to be a method capable of producing the product efficiently, economically and inexpensively on the industrial scale.

To produce norbornane dimethylene amines economically and inexpensively by hydrogenation of norbornane dicarbonitriles in the industrial scale, it is essential for the life of the catalyst used for hydrogenation to be long. In the prior art methods, however, the life of the catalyst cannot be sufficiently long, as described above, and even in the method of using a large amount of solvent and water, the life of the catalyst is still unsatisfactory.

The object of the present invention is to provide a process for producing the desired norbornane dimethylene amines efficiently, economically and inexpensively with the sufficiently longer life of the catalyst used for the reaction than in the prior art described above.

SUMMARY OF THE INVENTION

As a result of intensive study for solving the above-described problem in the hydrogenation of norbornane dicarbonitriles, the present inventors found that the problem can be solved in only the case where the hydrogenation is conducted by particularly using a Raney cobalt catalyst containing manganese in the presence of water in an amount within a specified range, and thus the present invention was completed.

That is, the present invention encompasses:

(1) A process for producing norbornane dimethylene amines represented by formula (II):

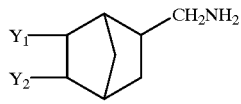

wherein $Y_1$ and $Y_2$ represent H or $CH_2NH_2$ and are not the same, wherein norbornane dicarbonitriles represented by formula (I):

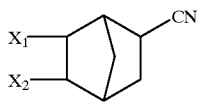

wherein $X_1$ and $X_2$ represent H or CN and are not the same, are hydrogenated by using a Raney cobalt catalyst containing one or more metals, particularly manganese which is or are selected from the group consisting of metals in groups Ib, IVa, IVb, Va, VIa, VIIa and VIII in the periodic table, in the presence of water in an amount of 0.1 to 1.5 moles per mole of the norbornane dicarbonitriles;

(2) The process according to the above item (1), wherein the hydrogenation is carried out in the presence of ammonia;

(3) The process according to the above item (2), wherein the amount of ammonia is 0.05 to 5 moles per mole of the norbornane dicarbonitriles;

(4) The process according to any one of the above items (1) to (3), wherein the amount of the catalyst is 0.1 to 10% by weight relative to the norbornane dicarbonitriles;

(5) The process according to any one of the above items (1) to (4), wherein the temperature for the hydrogenation is from 50 to 250° C.; and (6) The process according to any one of the above items (1) to (5), wherein the pressure for the hydrogenation is from 0.5 to 20 MPaG.

According to the present invention, there can be provided an industrially extremely useful process wherein norbornane dimethylene amines can be produced inexpensively with a long life of the catalyst and in the presence of extremely smaller amounts of ammonia, the catalyst and the solvent used in hydrogenation than in the prior art method.

DETAILED DESCRIPTION OF THE PREFERRED EMBODIMENTS

In the present invention, the norbornane dicarbonitriles as a starting material are compounds represented by formula (I) above, which include 2,5-norbornane dicarbonitrile, 2,6-norbornane dicarbonitrile, and a mixture of these compounds. Furhter these norbornane dicarbonitriles have stereoisomers, and any of these stereoisomers and a mixture thereof can also be used as the starting material in the present invention.

The norbornane dicarbonitriles described above can be obtained for example by a method of adding hydrogen cyanide to bicyclo[2.2.1]-5-heptene-2-carbonitrile in the presence of a nickel catalyst and triphenyl phosphate, as described in Japanese patent publication No. (JP-B) 7-94422.

In the present invention, the hydrogenation of norbornane dicarbonitriles is carried out preferably in the presence of ammonia. This ammonia has the function of improving selectivity by inhibiting formation of high-boiling byproducts such as secondary amines, tertiary amines or polyamines other than the desired norbornane dimethylene amines. For inhibiting formation of these high-boiling byproducts, preventing the reduction of the rate of hydrogenation, and facilitating the treatment or recovery of ammonia after the reaction, the amount of ammonia used is preferably in the range of 0.05 to 5 moles, more preferably 0.1 to 2.5 moles per mole of the starting norbornane dicarbonitriles.

The catalyst used in the present invention is a Raney cobalt catalyst containing one or more metals selected from the group consisting of metals of groups Ib, IVa, IVb, Va, VIa, VIIa and VIII in the periodic table, and preferably these metals are silver and copper in group Ib, titanium in group IVa, tin and lead in group IVb, vanadium in group Va, chromium, molybdenum and tungsten in group VIa, manganese in group VIIa and iron in group VIII, among which manganese is particularly preferable.

The catalyst containing manganese is a Raney cobalt catalyst containing manganese in an amount of 0.1 to 15% by weight, more preferably 0.5 to 10% by weight, and a catalyst obtained by alkali-development of Raney cobalt alloy powder containing manganese in a usual manner (e.g., Catalytic Engineering, vol. 10, Catalyst Handbook Classified by Element, page 528) can be used.

The amount of the catalyst charged into a reaction vessel is not particularly limited, but from the viewpoint of maintaining good fluidity of the reaction solution and simultaneously reducing the catalyst cost, the catalyst is used preferably in an amount of up to about 10% by weight, more specifically 0.1 to 10% by weight, relative to the starting norbornane dicarbonitriles.

For adding the catalyst to the reaction vessel, the total amount of the catalyst used may be added in one portion, but for controlling the chemical poisoning of the catalyst, it is preferable that the catalyst is added first in an amount necessary for one reaction and then added successively every repeated reaction.

The hydrogenation in the present invention is carried out in the presence of water. The amount of water used is preferably in the range of 0.1 to 1.5 moles, more preferably in the range of 0.2 to 1.5 moles, relative to 1 mole of the starting norbornane dicarbonitriles. If its amount is less than 0.1 mole, a sufficient life of the catalyst can hardly be achieved. Its amount of more than 1.5 moles is not preferable because byproducts such as amide derivatives other than the desired product are formed in a significantly large amount, and either because much energy is necessary in the steps of dehydration and purification after the reaction. So the reaction is conducted preferably in the presence of water in an amount within the range defined above.

The temperature for carrying out the hydrogenation in the present invention is preferably in the range of 50 to 250° C., more preferably in the range of 80 to 200° C. for keeping good productivity of norbornane dimethylene amines and simultaneously suppressing formation of byproducts.

It is preferable that hydrogen used in the hydrogenation is usually of 100% purity, but gases inert to the reaction, such as nitrogen, argon, helium or methane may be contained therein. The pressure during hydrogenation is preferably in the range of 0.5 to 20 MPaG, more preferably in the range of 1 to 10 MPaG. At a pressure of less than 0.5 MPaG, it will take a lot of time to complete the hydrogenation, thus worsening the productivity of the desired norbornane dimethylene amines. A pressure of more than 20 MPaG is not preferable because the increase of the pressure brings about virtually no effect, merely resulting in higher costs for construction of high-pressure facilities.

The hydrogenation in the present invention can also be carried out without using a solvent, but because the norbornane dicarbonitriles as the starting material are relatively highly viscous, a solvent may be used to improve operability, fluidity of the catalyst in the reaction vessel and others. The usable solvent shall be a compound inert to this hydrogenation reaction, and preferable examples include aromatic hydrocarbons such as benzene, toluene, xylene, ethyl benzene, diethyl benzene, mesitylene etc., alcohols such as methanol, ethanol, 1-propanol, 2-propanol, 1-butanol, 2-butanol etc., and analogous compounds thereto.

Further, when the above-described solvent is used, it can be used in an optional amount, but its amount is preferably in the range of up to 50 by weight, more preferably in the range of up to 20% by weight, most preferably in the range of up to 10% by weight relative to the starting norbornane dicarbonitriles in order to maintain good productivity of the resulting norbornane dimethylene amines and to lower the energy for removal of the solvent by distillation.

In the present invention, the reaction system for hydrogenation of norbornane dicarbonitriles is not particularly limited, and the hydrogenation can be carried out in any system such as a batch system, a semi-batch system, or a flow system.

EXAMPLES

Next, the usefulness of the present invention is described in further detail with reference to Examples. Hereinafter, analysis of a reaction solution was conducted by gas chromatography.

Example 1

An autoclave made of stainless steel having an internal volume of 0.5 L with an electromagnetic stirrer was charged with 304 g of norbornane dicarbonitriles solution (1.93 mol of norbornane dicarbonitriles) containing about 7% by weight of toluene, 24.9 g (1.38 mol) of water, and 1.5 g (dry weight) of a Raney cobalt catalyst (Co, 75.7% by weight; Al, 2.7% by weight; Mn, 1.5% by weight) obtained by developing a Co—Al alloy containing manganese. The system was purged sufficiently by nitrogen and then the netrogen was replaced by hydrogen, and 10.2 g (0.6 mol) of liquid ammonia was injected thereto. Then, hydrogen was introduced until the pressure in the autoclave reached 2.5 MPaG, and the mixture was heated to 120° C. under stirring to initiate hydrogenation reaction. Because the pressure in the autoclave was reduced as the reaction proceeded, hydrogen was fed continuously such that the pressure was kept at 3.4 MPaG, while the liquid temperature was kept at 120° C., and the hydrogenation reaction was carried out for 8 hours.

After the reaction, the autoclave was cooled to room temperature, and the hydrogen and ammonia in the gaseous phase were released. The precipitated catalyst was left in the autoclave, and the supernatant in the reaction solution was taken out. Another norbornane dicarbonitriles solution, ammonia and water were charged into the autoclave in the same amounts as above and subjected to the hydrogenation reaction. This operation was conducted repeatedly 20 times without adding any further catalyst.

As a result, the conversion of norbornane dicarbonitriles and the yield of norbornane dimethylene amines in the first reaction were 100% and 94.5% respectively, and the conversion and the yield in the 20th reaction were 100% and 94.3% respectively, and no deterioration in the catalyst was observed. Further, the yield of an amide derivative where cyano groups in the starting norbornane dicarbonitriles had been hydrolyzed was 0.4% in the first reaction, and there was no change in the yield even in the 20th reaction.

Example 2

Following the procedure in Example 1, the operation of charging norbornane dicarbonitriles solution, ammonia and water in the same amounts as every reaction in Example 1 and then performing the hydrogenation reaction was repeatedly carried out 50 times in the same manner as in Example 1. The catalyst was added by 0.5 g in the 21st, 31st, and 41st reactions, respectively.

As a result, the conversion of norbornane dicarbonitriles and the yield of norbornane dimethylene amines in the 21st reaction were 100% and 94.3% respectively, and the conversion and the yield in the 50th reaction were 100% and 94.0% respectively, and no deterioration in the catalyst was observed. Further, the yield of an amide derivative where cyano groups in the starting norbornane dicarbonitriles had been hydrolyzed was 0.4% in the 21st reaction and 0.5% in the 50th reaction.

Example 3

An autoclave made of stainless steel having an internal volume of 0.5 L with an electromagnetic stirrer was charged with 304 g of norbornane dicarbonitriles solution (1.93 mol of norbornane dicarbonitriles) containing about 7% by weight of toluene, 49.6 g (2.75 mol) of water, and 1.5 g of a Raney cobalt catalyst (Co, 75.7% by weight; Al, 2.7% by weight; Mn, 1.5% by weight) obtained by developing a Co—Al alloy containing manganese. The system was purged sufficiently by nitrogen and then the nitrogen was replaced by hydrogen, and 10.2 g (0.6mol) of liquid ammoniawas injected thereto. Then, hydrogen was introduced until the pressure in the autoclave reached 3.9 MPaG, and the mixture was heated to 120° C. under stirring to initiate hydrogenation reaction. Because the pressure in the autoclave was reduced as the reaction proceeded, hydrogen was fed continuously such that the pressure was kept at 4.9 MPaG, while the liquid temperature was kept at 120° C., and the hydrogenation reaction was carried out for 8 hours.

After the reaction, the autoclave was cooled to room temperature, and the hydrogen and ammonia in the gaseous phase were released. The precipitated catalyst was left in the autoclave, and the supernatant in the reaction solution was taken out. Another norbornane dicarbonitriles solution, ammonia and water were charged into the autoclave in the same amounts as above and subjected to the hydrogenation reaction. This operation was conducted repeatedly 20 times without adding any further catalyst.

As a result, the conversion of norbornane dicarbonitriles and the yield of norbornane dimethylene amines in the first reaction were 100% and 94.6% respectively, and the conversion and the yield in the 20th reaction were 100% and 93.3% respectively, and no deterioration in the catalyst was observed. Further, the yield of an amide derivative where cyano groups in the starting norbornane dicarbonitriles had been hydrolyzed was 1.8% in the first reaction and 2.1% in the 20th reaction.

Example 4

The same operation as in Example 3 was carried out except that the amount of water charged into the autoclave was 12.3 g (0.68 mol) and the hydrogenation reaction was cattied out at the liquid temperature of 140° C. for 3 hours.

As a result, the conversion of norbornane dicarbonitriles and the yield of norbornane dimethylene amines in the first reaction were 100% and 93.8% respectively, and the conversion and the yield in the 20th reaction were 100% and 91.1% respectively, and no deterioration in the catalyst was observed. Further, the yield of an amide derivative where cyano groups in the starting norbornane dicarbonitriles had been hydrolyzed was 0.4% in the first reaction, and there was no change in the yield even in the 20th reaction.

Example 5

An autoclave made of stainless steel having an internal volume of 0.5 L with an electromagnetic stirrer was charged with 304 g of norbornane dicarbonitriles solution (1.93 mol of norbornane dicarbonitriles) containing about 7% by weight of toluene, 5.2 g (0.29 mol) of water, and 1.5 g of a Raney cobalt catalyst (Co, 75.7% by weight; Al, 2.7% by weight; (7 Mn, 1.5% by weight) obtained by developing a Co—Al alloy containing manganese. The system was purged sufficiently by nitrogen and then the nitrogen was replaced by hydrogen, and 10.2 g (0.6mol) of liquid ammoniawas injected thereto. Then, hydrogen was introduced until the pressure in the autoclave reached 6.9 MPaG, and the mixture was heated to 120° C. under stirring to initiate hydrogenation reaction. Because the pressure in the autoclave was reduced as the reaction proceeded, hydrogen was fed continuously such that the pressure was kept at 7.8 MPaG, while the liquid temperature was kept at 120° C., and the hydrogenation reaction was carried out for 3 hours.

After the reaction, the autoclave was cooled to room temperature, and the hydrogen and ammonia in the gaseous phase were released. The precipitated catalyst was left in the autoclave, and the supernatant in the reaction solution was taken out. Another norbornane dicarbonitriles solution, ammonia and water were charged into the autoclave in the same amounts as above and subjected to the hydrogenation reaction. This operation was conducted repeatedly 20 times without adding any further catalyst.

As a result, the conversion of norbornane dicarbonitriles and the yield of norbornane dimethylene amines in the first reaction were 100% and 95.1% respectively, and the conversion and the yield in the 20th reaction were 100% and 90.2% respectively, and no deterioration in the catalyst was observed. Further, the yield of an amide derivative where cyano groups in the starting norbornane dicarbonitriles had been hydrolyzed was 0.3% in the first reaction, and there was no change in the yield even in the 20th reaction.

Example 6

The same operation as in Example 1 was carried out except that the amount of the catalyst charged into the autoclave was 4.5 g, and the reaction was carried out for 3 hours.

As a result, the conversion of norbornane dicarbonitriles and the yield of norbornane dimethylene amines in the first reaction were 100% and 94.5% respectively, and the conversion and the yield in the 20th reaction were 100% and 94.4% respectively, and no deterioration in the catalyst was observed. Further, the yield of an amide derivative where cyano groups in the starting norbornane dicarbonitriles had been hydrolyzed was 0.6% in the first reaction, and there was no change in the yield even in the 20th reaction.

Example 7

The same operation as in Example 1 was carried out except that the norbornane dicarbonitriles charged into the autoclave was free of toluene and the hydrogenation reaction was carried out at the liquid temperature of 160° C. for 4 hours.

As a result, the conversion of norbornane dicarbonitriles and the yield of norbornane dimethylene amines in the first reaction were 100% and 93.5% respectively, and the conversion and the yield in the 20th reaction were 100% and 93.2% respectively, and no deterioration in the catalyst was observed. Further, the yield of an amide derivative where cyano groups in the starting norbornane dicarbonitriles had been hydrolyzed was 0.4% in the first reaction, and there was no change in the yield even in the 20th reaction.

Example 8

The same operation as in Example 1 was carried out except that the amount of the catalyst charged into the autoclave was 4.5 g, and the liquid temperature for the hydrogenation reaction was 100° C.

As a result, the conversion of norbornane dicarbonitriles and the yield of norbornane dimethylene amines in the first reaction were 100% and 96.2% respectively, and the conversion and the yield in the 20th reaction were 100% and 95.6% respectively, and no deterioration in the catalyst was observed. Further, the yield of an amide derivative where cyano groups in the starting norbornane dicarbonitriles had been hydrolyzed was 0.4% in the first reaction, and there was no change in the yield even in the 20th reaction.

Example 9

An autoclave made of stainless steel having an internal volume of 0.5 L with an electromagnetic stirrer was charged with 304 g of norbornane dicarbonitrile solution (1.93 mol of norbornane dicarbonitriles) containing about 7% by weight of toluene, 24.9 g (1.38 mol) of water, and 4.5 g of a Raney cobalt catalyst (Co, 68.5% by weight; Al, 3.1% by weight; Mn, 5.5% by weight) obtained by developing a Co—Al alloy containing manganese. The system was purged sufficiently by nitrogen and then the netrogen was replaced by hydrogen, and 10.2 g (0.6 mol) of liquid ammonia was injected thereto. Then, hydrogen was introduced until the pressure in the autoclave reached 3.9 MPaG, and the mixture was heated to 140° C. under stirring to initiate hydrogenation reaction. Because the pressure in the autoclave was reduced as the reaction proceeded, hydrogen was fed continuously such that the pressure was kept at 4.9 MPaG, while the liquid temperature was kept at 140° C., and the hydrogenation reaction was carried out for 2 hours.

After the reaction, the autoclave was cooled to room temperature, and the hydrogen and ammonia in the gaseous phase were released. The precipitated catalyst was left in the autoclave, and the supernatant in the reaction solution was taken out. Another norbornane dicarbonitrile solution, ammonia and water were charged into the autoclave in the same amounts as above and subjected to the hydrogenation reaction. This operation was conducted repeatedly 20 times without adding any further catalyst.

As a result, the conversion of norbornane dicarbonitriles and the yield of norbornane dimethylene amines in the first reaction were 100% and 93.3% respectively, and the conversion and the yield in the 20th reaction were 100% and 93.1% respectively, and no deterioration in the catalyst was observed. Further, the yield of an amide derivative where cyano groups in the starting norbornane dicarbonitriles had been hydrolyzed was 0.8% in the first reaction, and there was no change in the yield even in the 20th reaction.

Example 10 The same operation as in Example 9 was carried out except that the amount of the catalyst charged into the autoclave was 0.6 g and the hydrogenation reaction was carried out at the liquid temperature of 180° C. for 8 hours.

As a result, the conversion of norbornane dicarbonitriles and the yield of norbornane dimethylene amines in the first reaction were 100% and 92.2% respectively, and the conversion and the yield in the 20th reaction were 100% and 91.4% respectively, and no deterioration in the catalyst was observed. Further, the yield of an amide derivative where cyano groups in the starting norbornane dicarbonitriles had been hydrolyzed was 1.0% in the first reaction, and there was no change in the yield even in the 20th reaction.

Example 11

The same operation as in Example 9 was carried out except that the amount of liquid ammonia charged into the autoclave was 3.6 g (0.2 mol), and the reaction was carried out for 3 hours.

As a result, the conversion of norbornane dicarbonitriles and the yield of norbornane dimethylene amines in the first reaction were 100% and 91.2% respectively, and the conversion and the yield in the 20th reaction were 100% and 90.7% respectively, and no deterioration in the catalyst was observed. Further, the yield of an amide derivative where cyano groups in the starting norbornane dicarbonitriles had been hydrolyzed was 0.6% in the first reaction, and there was no change in the yield even in the 20th reaction.

Example 12

An autoclave made of stainless steel having an internal volume of 0.5 L with an electromagnetic stirrer was charged with 304 g of norbornane dicarbonitrile solution (1.93 mol of norbornane dicarbonitriles) containing about 7% by weight of toluene, 24.9 g (1.38 mol) of water, and 4.5 g of a Raney cobalt catalyst (Co, 64.0% by weight; Al, 3.3% by weight; Mn, 8.5% by weight) obtained by developing a Co—Al alloy containing manganese. The system was purged sufficiently by nitrogen and then the nitrogen was replaced by hydrogen, and 30.6 g (1.8 mol) of liquid ammonia was injected. Then, hydrogen was introduced until the pressure in the autoclave reached 2.0 MPaG, and the mixture was heated to 140° C. under stirring to initiate hydrogenation reaction. Because the pressure in the autoclave was reduced as the reaction proceeded, hydrogen was fed continuously such that the pressure was kept at 2.5 MPaG, while the liquid temperature was kept at 140° C., and the hydrogenation reaction was carried out for 5 hours.

After the reaction, the autoclave was cooled to room temperature, and the hydrogen and ammonia in the gaseous phase were released. The precipitated catalyst was left in the autoclave, and the supernatant in the reaction solution was taken out. Another norbornane dicarbonitrile solution, ammonia and water were charged into the autoclave in the same amounts as above and subjected to the hydrogenation reaction. This operation was conducted repeatedly 20 times without adding any further catalyst.

As a result, the conversion of norbornane dicarbonitriles and the yield of norbornane dimethylene amines in the first reaction were 100% and 92.2% respectively, and the conversion and the yield in the 20th reaction were 100% and 92.1% respectively, and no deterioration in the catalyst was observed. Further, the yield of an amide derivative where cyano groups in the starting norbornane dicarbonitriles had been hydrolyzed was 0.7% in the first reaction, and there was no change in the yield even in the 20th reaction.

Example 13

The same operation as in Example 9 was carried out except that 4.5 g of a Raney cobalt catalyst (Co, 76.0% by weight; Al, 4.0% by weight; Mn, 0.2% by weight) obtained by developing a Co—Al alloy containing manganese was used as the catalyst charged into the autoclave, the amount of liquid ammonia was 65.8 g (3.9 mol), and the reaction was carried out for 4 hours.

As a result, the conversion of norbornane dicarbonitriles and the yield of norbornane dimethylene amines in the first reaction were 100% and 93.8% respectively, and the conversion and the yield in the 20th reaction were 100% and 93.5% respectively, and no deterioration in the catalyst was observed. Further, the yield of an amide derivative where cyano groups in the starting norbornane dicarbonitriles had been hydrolyzed was 0.9% in the first reaction, and there was no change in the yield even in the 20th reaction.

Example 14

The same operation as in Example 9 was carried out except that 4.5 g of a Raney cobalt catalyst (Co, 57.5% by weight; Al, 3.7% by weight; Mn, 11.7% by weight) obtained by developing a Co—Al alloy containing manganese was used as the catalyst charged into the autoclave, the amount of liquid ammonia was 131.6 g (7.7 mol), and the reaction was carried out for 6 hours.

As a result, the conversion of norbornane dicarbonitriles and the yield of norbornane dimethylene amines in the first reaction were 100% and 94.1% respectively, and the conversion and the yield in the 20th reaction were 100% and 93.9% respectively, and no deterioration in the catalyst was observed. Further, the yield of an amide derivative where cyano groups in the starting norbornane dicarbonitriles had been hydrolyzed was 1.0% in the first reaction, and there was no change in the yield even in the 20th reaction.

Comparative Example 1

The same operation as in Example 1 was carried out except that the hydrogenation reaction was performed without charging water into the autoclave.

As a result, the conversion of norbornane dicarbonitriles and the yield of norbornane dimethylene amines in the first reaction were 100% and 93.2%, respectively, but in the third reaction, the yield was 37.3% with the starting norbornane dicarbonitriles still remained, and the deterioration in the catalyst was observed.

Comparative Example 2

The same operation as in Example 1 was carried out except that the amount of water charged into the autoclave was 1.7 g (0.1 mol).

As a result, the conversion of norbornane dicarbonitriles and the yield of norbornane dimethylene amines in the first reaction were 100% and 93.3%, respectively, but in the fifth reaction, the yield was 42.5% with the starting norbornane dicarbonitriles still remained, and the deterioration in the catalyst was observed.

Comparative Example 3

The same operation as in Example 1 was carried out except that the amount of water charged into the autoclave was 70.1 g (3.9 mol).

As a result, the conversion of norbornane dicarbonitriles and the yield of norbornane dimethylene amines in the first reaction were 100% and 81.6%, respectively, and the conversion and the yield in the 20th reaction were 100% and 79.0% respectively, indicating a low yield. Further, the yield of an amide derivative where cyano groups in the starting norbornane dicarbonitriles had been hydrolyzed was as high as 9.7% in the first reaction and 11.9% in the 20th reaction.

Comparative Example 4

The same operation as in Example 9 was carried out except that a Raney cobalt catalyst (Co, 76.9% by weight; Al, 4.2% by weight) obtained by developing a manganese-free Co—Al alloy was used as the catalyst charged into the autoclave, and the reaction was carried out for 4 hours.

As a result, the conversion of norbornane dicarbonitriles and the yield of norbornane dimethylene amines in the first reaction were 100% and 89.8%, respectively, but in the fifth reaction, the yield was 47.6% with the starting norbornane dicarbonitriles still remained, and the deterioration in the catalyst was observed.

As can be seen from the foregoing description, particularly Examples 1 to 14 and Comparative Examples 1 to 4, an extremely long life of the catalyst can be achieved in the process of the present invention wherein the hydrogenation of norbornane dicarbonitriles is carried out by using a Raney cobalt catalyst containing manganese in the presence of water in an amount of 0.1 to 1.5 moles per mole of the norbornane dicarbonitriles.

What is claimed is:

1. A process for producing norbornane dimethylene amines represented by formula (II):

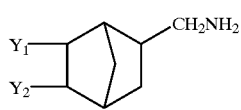

(II)

wherein $Y_1$ and $Y_2$ represent H or $CH_2NH_2$ and are not the same, wherein norbornane dicarbonitriles represented by formula (I):

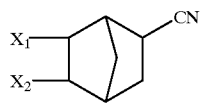

(I)

wherein $X_1$ and $X_2$ represent H or CN and are not the same, are hydrogenated by using a Raney cobalt catalyst containing one or more metals selected from the group consisting of metals in the groups Ib, IVa, IVb, Va, VIa, VIIa and VIII, in the presence of water in an amount of 0.1 to 1.5 moles per mole of the norbornane dicarbonitriles.

2. The process for producing norbornane dimethylene amines according to claim 1, wherein the metal in group Ib is copper or silver.

3. The process for producing norbornane dimethylene amines according to claim 1, wherein the metal in group IVa is titanium.

4. The process for producing norbornane dimethylene amines according to claim 1, wherein the metal in group IVb is tin or lead.

5. The process for producing norbornane dimethylene amines according to claim 1, wherein the metal in group Va is vanadium.

6. The process for producing norbornane dimethylene amines according to claim 1, wherein the metal in group VIa is chromium, molybdenum or tungsten.

7. The process for producing norbornane dimethylene amines according to claim 1, wherein the metal in group VIIa is manganese.

8. The process for producing norbornane dimethylene amines according to claim 1, wherein the metal in group VIII is iron.

9. The process for producing norbornane dimethylene amines according to any one of claim 1, wherein the hydrogenation is carried out in the presence of ammonia.

10. The process for producing norbornane dimethylene amines according to claim 7, wherein the hydrogenation is carried out in the presence of ammonia.

11. The process for producing norbornane dimethylene amines according to claim 1, wherein the amount of ammonia is 0.05 to 5 moles per mole of the norbornane dicarbonitriles.

12. The process for producing norbornane dimethylene amines according to claim 9, wherein the amount of ammonia is 0.05 to 5 moles per mole of the norbornane dicarbonitriles.

13. The process for producing norbornane dimethylene amines according to claim 1, wherein the amount of the catalyst is 0.1 to 10% by weight relative to the norbornane dicarbonitriles.

14. The process for producing norbornane dimethylene amines according to claim 12, wherein the amount of the catalyst is 0.1 to 10% by weight relative to the norbornane dicarbonitriles.

15. The process for producing norbornane dimethylene amines according to claim 1, wherein the temperature for the hydrogenation is from 50 to 250° C.

16. The process for producing norbornane dimethylene amines according to claim 12, wherein the temperature for the hydrogenation is from 50 to 250° C.

17. The process for producing norbornane dimethylene amines according to claim 13, wherein the temperature for the hydrogenation is from 50 to 250° C.

18. The process for producing norbornane dimethylene amines according to claim 14, wherein the temperature for the hydrogenation is from 50 to 250° C.

19. The process for producing norbornane dimethylene amines according to claim 1, wherein the pressure for the hydrogenation is from 0.5 to 20 MPaG.

20. The process for producing norbornane dimethylene amines according to claim 12, wherein the pressure for the hydrogenation is from 0.5 to 20 MPaG.

21. The process for producing norbornane dimethylene amines according to claim 13, wherein the pressure for the hydrogenation is from 0.5 to 20 MPaG.

22. The process for producing norbornane dimethylene amines according to claim 14, wherein the pressure for the hydrogenation is from 0.5 to 20 MPaG.

23. The process for producing norbornane dimethylene amines according to claim 15, wherein the pressure for the hydrogenation is from 0.5 to 20 MPaG.

24. The process for producing norbornane dimethylene amines according to claim 16, wherein the pressure for the hydrogenation is from 0.5 to 20 MPaG.

25. The process for producing norbornane dimethylene amines according to claim 17, wherein the pressure for the hydrogenation is from 0.5 to 20 MPaG.

26. The process for producing norbornane dimethylene amines according to claim 18, wherein the pressure for the hydrogenation is from 0.5 to 20 MPaG.

* * * * *